(12) United States Patent
Dowd et al.

(10) Patent No.: US 6,436,138 B1
(45) Date of Patent: Aug. 20, 2002

(54) PROCESS FOR PRODUCING FLEXIBLE SHEETS FROM DEMINERALIZED, ELONGATE, BONE PARTICLES

(75) Inventors: Michael Dowd, Eastampton; Nelson L. Scarborough, Wayside; Mark Daugherty, Allenwood, all of NJ (US); Jack McMickle, Nazareth, PA (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/155,064

(22) PCT Filed: Jan. 16, 1997

(86) PCT No.: PCT/US97/00644

§ 371 (c)(1),
(2), (4) Date: Sep. 18, 1998

(87) PCT Pub. No.: WO97/25941

PCT Pub. Date: Jul. 24, 1997

Related U.S. Application Data

(60) Provisional application No. 60/010,127, filed on Jan. 17, 1996.

(51) Int. Cl.[7] ................................................ A61F 2/28
(52) U.S. Cl. ................ 623/16.11; 623/901; 623/23.61; 623/919
(58) Field of Search ........................... 623/16.11, 23.61, 623/23.63, 901, 919, 923; 600/36

(56) References Cited

U.S. PATENT DOCUMENTS

| | | | |
|---|---|---|---|
| 4,743,259 A | * 5/1988 | Bolander et al. | ............. 623/16 |
| 5,123,925 A | 6/1992 | Smestad et al. | |
| 5,171,574 A | * 12/1992 | Kuberasampath et al. | .. 424/423 |
| 5,306,304 A | 4/1994 | Gendler | |
| 5,314,476 A | 5/1994 | Prewett et al. | |
| 5,507,813 A | 4/1996 | Dowd et al. | |
| 5,531,791 A | * 7/1996 | Wolfinbarger, Jr. | .......... 623/16 |

* cited by examiner

Primary Examiner—Paul B. Prebilic
(74) Attorney, Agent, or Firm—Dilworth & Barese, LLP

(57) ABSTRACT

A process for fabricating shaped material from demineralized bone particles includes the steps of applying a liquid slurry of demineralized bone particles to a support, removing excess liquid form the demineralized bone particles to provide a cohering shaped mass of demineralized bone particles, and warming the shaped mass of demineralized bone particles at a predetermined temperature and for a predetermined time period. The resultant bone mass exhibits enhanced tensile strength and minimal bone particle disassociation upon rehydration thereby improving product handling and application at the operative site.

13 Claims, 6 Drawing Sheets

PROCESS FOR PRODUCING FLEXIBLE SHEETS FROM DEMINERALIZED, ELONGATE, BONE PARTICLES

REFERENCE TO RELATED APPLICATIONS

This application is a national stage application of PCT/US97/00644 filed Jan. 16, 1997 which claims priority to U.S. provisional application No. 60/010,127 filed Jan. 17, 1996.

BACKGROUND OF THE INVENTION

1. Field of the Invention

The present invention relates generally to surgically implanted materials fabricated from demineralized bone particles, and, more particularly, to such materials which are made up of a coherent shaped mass of elongate bone particles having an improved capacity to maintain its cohesive properties and exhibiting minimal bone particle disassociation upon rehydration.

2. Description of Related Art

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein", *Orthopaedic Review*, Vol. XVII, No. 8, pp. 857–863 (August 1989). According to Habal et al., "Autologous Corticocancellous Bone Paste for Long Bone Discontinuity Defects: An Experimental Approach", *Annals of Plastic Surgery*, Vol. 15, No. 2, pp. 138–142 (August 1985), autogenous bone which has been granulated into a pastelike material and combined with autogenous blood has been used in the repair of long bone defects in dogs.

U.S. Pat. No. 5,073,373 discloses a deformable, shape-sustaining osteogenic composition, suitable as a filler for osseous defects, in which particles of demineralized bone are uniformly distributed within a carrier which is a liquid polyhydroxy compound such as glycerol. The vast majority of the demineralized bone particles possess random, irregular geometries with an average median length to median thickness ratio of from about 1:1 to about 3:1.

Commonly assigned U.S. Pat. No. 5,314,476 discloses a flowable osteogenic composition containing entangled demineralized bone particles of relatively high median length to median thickness ratio. The flowable osteogenic composition can possess a paste-like or putty-like consistency as well as a liquid or runny consistency.

Commonly assigned U.S. Pat. No. 5,507,813 to Dowd et al., the contents of which are incorporated herein by reference, discloses a surgically implantable shaped material fabricated from elongate bone particles. The shaped material, e.g., in the form of a sheet, is formed by applying a liquid slurry of elongate bone particles, e.g., filaments or fibers, to a porous support, draining excess liquid from the bone particles, optionally while applying a compressive force to the particles during and/or after drainage of the excess liquid, to provide a coherent, shaped wetted mass of bone particles and, optionally, drying the wetted mass. The material thus formed is relatively rigid when dry and, upon contact with a biocompatible liquid, e.g., water, saline solution, etc., becomes pliable and flexible.

Although the shaped bone implant disclosed in the Dowd et al. '813 patent has proven to be quite effective in the repair of bone defects, the present invention is directed to further improvements in the process of fabricating such implants.

SUMMARY OF THE INVENTION

Generally, the coherent shaped mass of demineralized bone particles produced in accordance with the principles of the present invention exhibit an enhanced capacity to retain its cohesive properties and experience minimal bone particle disassociation upon rehydration, thereby improving product handling and application at the operative site.

In a preferred embodiment, a process for fabricating shaped material from bone particles includes the steps of applying a liquid slurry of bone particles to a support, removing excess liquid from the bone particles to provide a coherent shaped mass of bone particles, and warming the shaped-mass of bone particles at a predetermined temperature and for a predetermined time period. Preferably, the bone particles are demineralized. The process may further include the step of drying, e.g., through lyophilization, the shaped-mass of demineralized bone particles subsequent to the step of warming. Preferably, a sheet of demineralized bone particles is produced.

BRIEF DESCRIPTION OF THE DRAWINGS

Preferred embodiments of the disclosure are described herein with reference to the drawings wherein.

DESCRIPTION OF THE PREFERRED EMBODIMENTS

Application of the shaped material of the present invention to the site of a bone defect, e.g., one resulting from injury, infection, malignancy or developmental malformation, leads to new bone ingrowth by one or more biological mechanisms such as osteogenesis, osteoconduction and/or osteoinduction or by one or more physical mechanisms such as constituting a physical barrier to soft tissue ingrowth, providing a support or scaffolding for new bone growth, etc.

The term "osteogenic" as applied to the material of this invention shall therefore be understood as referring to the ability of the material of this invention to participate in the process of new bone growth regardless of the mechanism(s) involved.

The term "coherent" as applied to the mass of elongate bone particles refers to the ability of the bone particles to adhere to each other either mechanically, e.g., by entanglement, or by use of a biocompatible adhesive whether the shaped material containing the bone particles is in the dry or wetted, e.g., hydrated, state.

The term "shaped" as applied to the bone material of this invention shall be understood as referring to a determined or regular form or configuration, in contrast to an indeterminate or vague form or configuration (as in the case of a "lump" or other solid mass of no special form) and is characteristic of such materials as sheets, plates, disks, cones, pins, screws, and the like.

The term "rigid" shall be understood to refer to the relatively stiff, inflexible and somewhat brittle nature of the shaped materials of this invention while in the dry, i.e., unwetted, state.

The term "flexible" shall be understood to refer to the ability of the shaped material to become pliable upon being wetted or hydrated with a suitable biocompatible liquid and thus more readily conformable to a bone repair site.

Figure 1:
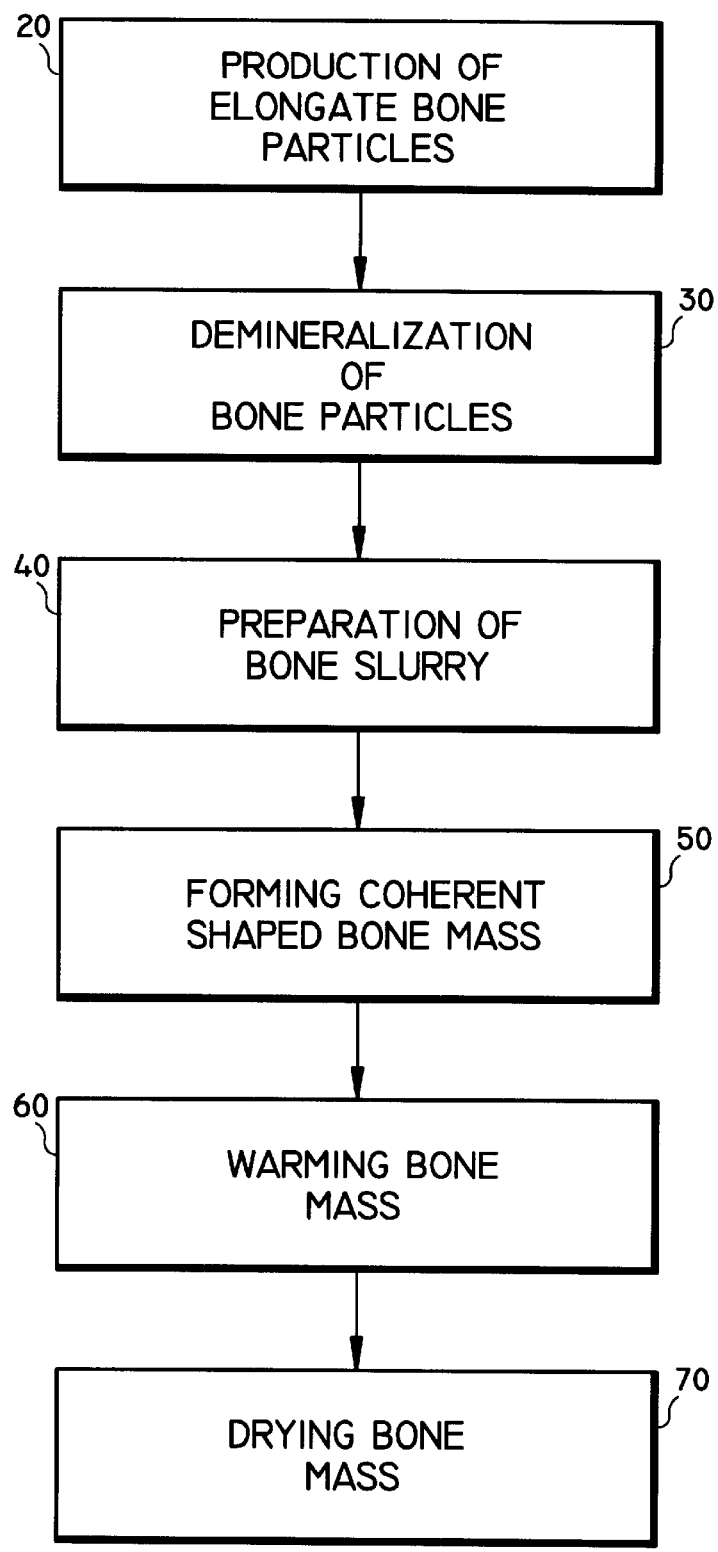
FIG. 1 is a flow diagram illustrating the preferred process for fabricating shaped material from demineralized bone particles in accordance with the principles of the present invention.

Referring now to FIG. 1, a flow chart of the process for forming a shaped material from demineralized bone particles in accordance with a preferred embodiment of the present invention is illustrated. The process generally entails six (6) steps to form the desired shaped bone mass which, in the preferred embodiment, is a sheet of demineralized bone particles.

Production of Elongate Bone Particles The first step of the process is the production of bone particles 20. Such particles can be readily obtained by any one of several methods, e.g., by milling or shaving the surface of an entire bone or relatively large section of bone. Employing a milling technique, particles ranging in median length from about 2 up to about 200 mm or more (as in the case of the long bones), in median thickness from about 0.05 to about 2 mm and in median width from about 1 to about 20 mm can be readily obtained. Another procedure for obtaining the elongate bone particles herein, particularly useful for pieces of bone of up to about 100 mm in length, is the Cortical Bone Shredding Mill available from Os Processing Inc., 3303 Carnegie Avenue, Cleveland, Ohio 44115. Use of this bone mill results in the production of long, thin strips which quickly curl lengthwise to provide tubular-like bone particles. Another apparatus and procedure utilized for obtaining bone particles is disclosed in commonly assigned U.S. patent application Ser. No. 08/560,213, filed Nov. 21, 1995.

Depending on the procedure employed for producing the elongate bone particles, one can obtain a mass of bone particles containing a specific weight percent, a median length and a median thickness. The aforementioned Dowd '813 patent discloses the use of bone particles containing at least about 60 weight percent, preferably at least about 70 weight percent and most preferably at least about 80 weight percent of bone particles possessing a median length of from about 2 to about 200 mm or more and preferably from about 10 to about 100 mm, a median thickness of from about 0.05 to about 2 mm and preferably from about 0.2 to about 1 mm and a median width of from about 1 mm to about 20 mm and preferably from about 2 to about 5 mm. These bone particles can possess a median length to median thickness ratio of at least about 50:1 up to about 500:1 or more and preferably from about 50:1 to about 100:1 and a median length to median width ratio of from about 10:1 to about 200:1 and preferably from about 50:1 to about 100:1.

If desired, the mass of elongate bone particles can be graded into different sizes to reduce or eliminate any less desirable size(s) of particles which may be present. In overall appearance, the elongate bone particles can be described as filaments, fibers, threads, slender or narrow strips, etc. As already noted and depending on the manner in which they are produced, these elongate particles may have a tendency to curl to provide tubular-like particles. The bone particles can be obtained from cortical, cancellous and/or corticocancellous bone which may be of autogenous, allogenic and/or xenogeneic origin.

Demineralization

With reference again to the flow chart of FIG. 1, following the shaving, milling or other technique, the elongate bone particles are subjected to a demineralization process 30 to reduce their inorganic content to a low level, e.g., to not more than about 5% by weight of residual calcium and preferably to not more than about 0.5% by weight residual calcium. Demineralization of the bone particles will ordinarily result in producing particles of slightly smaller dimensions.

The elongate bone particles can be demineralized in accordance with known and conventional procedures. In a preferred demineralization procedure, the elongate bone particles are subjected to a defatting/disinfecting step which is followed by an acid demineralization step. A preferred defatting/disinfectant solution is an aqueous solution of ethanol, the ethanol being a good solvent for lipids and the water being a good hydrophilic carrier to enable the solution to penetrate more deeply into the bone particles. The aqueous ethanol solution also disinfects the bone by killing vegetative microorganisms and viruses. Ordinarily at least about 10 to about 40 weight percent by weight of water (i.e., about 60 to about 90 weight percent of defatting agent such as alcohol) should be present in the defatting/disinfecting solution to produce optimal lipid removal and disinfection within the shortest period of time. The preferred concentration range of the defatting solution is from about 60 to about 85 weight percent alcohol and most preferably about 70 weight percent alcohol. Following defatting, the bone particles are immersed in acid over time to effect their demineralization. Acids which can be employed in this step include inorganic acids such as hydrochloric acid and organic acids such as peracetic acid. After acid treatment, the demineralized bone particles are rinsed with sterile water for injection to remove residual amounts of acid and thereby raise the pH. At this point some entanglement of the wet demineralized bone particles will result. The wet demineralized bone particles can then be immediately shaped into a shaped osteogenic material in accordance with the method of this invention or stored under aseptic conditions, advantageously in a lyophilized state, for processing at a later time.

The elongate bone particles can be admixed with one or more substances such as adhesives, fillers, plasticizers, flexibilizing agents, biostatic/biocidal agents, surface active agents, binding and bonding agents, fillers, and the like, prior to, during, or after shaping the particles into a desired configuration. Suitable adhesives, binding agents and bonding agents include acrylic resins, cellulosics, bioresorbable polymers such as polyglycolide, polylactide, glycolide-lactide copolymer, etc. Suitable fillers include bone powder, demineralized bone powder, hydroxyapatite, etc. Suitable plasticizers and flexibilizing agents include liquid polyhydroxy compounds such as glycerol, monacetin, diacetin, etc. Suitable biostatic/biocidal agents include antibiotics, povidone, sugars, etc. Suitable surface active agents include the biocompatible nonionic, cationic, anionic and amphoteric surfactants.

If desired, the bone particles can be modified in one or more ways, e.g., their protein content can be augmented or modified as described in U.S. Pat. Nos. 4,743,259 and 4,902,296. Any of a variety of medically and/or surgically useful substances can be incorporated in, or associated with, the bone particles either before, during or after fabrication of the shaped articles disclosed herein. Thus, e.g., one or more of such substances can be introduced into the demineralized bone particles, e.g., by soaking or immersing the bone particles in a solution or dispersion of the desired substance (s).

Medically/surgically useful substances which can be readily combined with the demineralized bone particles and/or osteogenic material of this invention include, e.g., collagen, insoluble collagen derivatives, etc., and soluble solids and/or liquids dissolved therein, e.g., antiviri-cides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; biocidal/biostatic sugars such as dextroal, glucose, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; antigenic agents; cytoskeletal agents; cartilage fragments, living cells such as chondrocytes, bone marrow cells, mesenchymal stem cells, natural extracts, tissue transplants, bone, demineralized bone powder, autogenous tissues such blood, serum, soft tissue, bone marrow, etc.; bioadhesives, bone morphogenic proteins (BMPs), transforming growth factor (TGF-beta), insulin-like growth factor (IGF-1); growth hormones such as somatotropin; bone digestors; antitumor agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

Preparation of Bone Slurry

With reference still to FIG. 1, subsequent to demineralization the next step 40 in the process involves the formation of the bone slurry from the demineralized product. Preferably, the bone particles are slurried in a suitable liquid, e.g., water, glycerol, organic protic solvent, aqueous solution, such as physiological saline, etc., and optionally containing one or more biocompatible ingredients such as adhesives, fillers, plasticizers, fertilizing agents, biostatic/ bioaidal agents, surface active agents, medically/surgically useful substances, etc . . . , and allowed to reach equilibrium.

Forming Coherent Shaped Bone Mass

Figure 2:
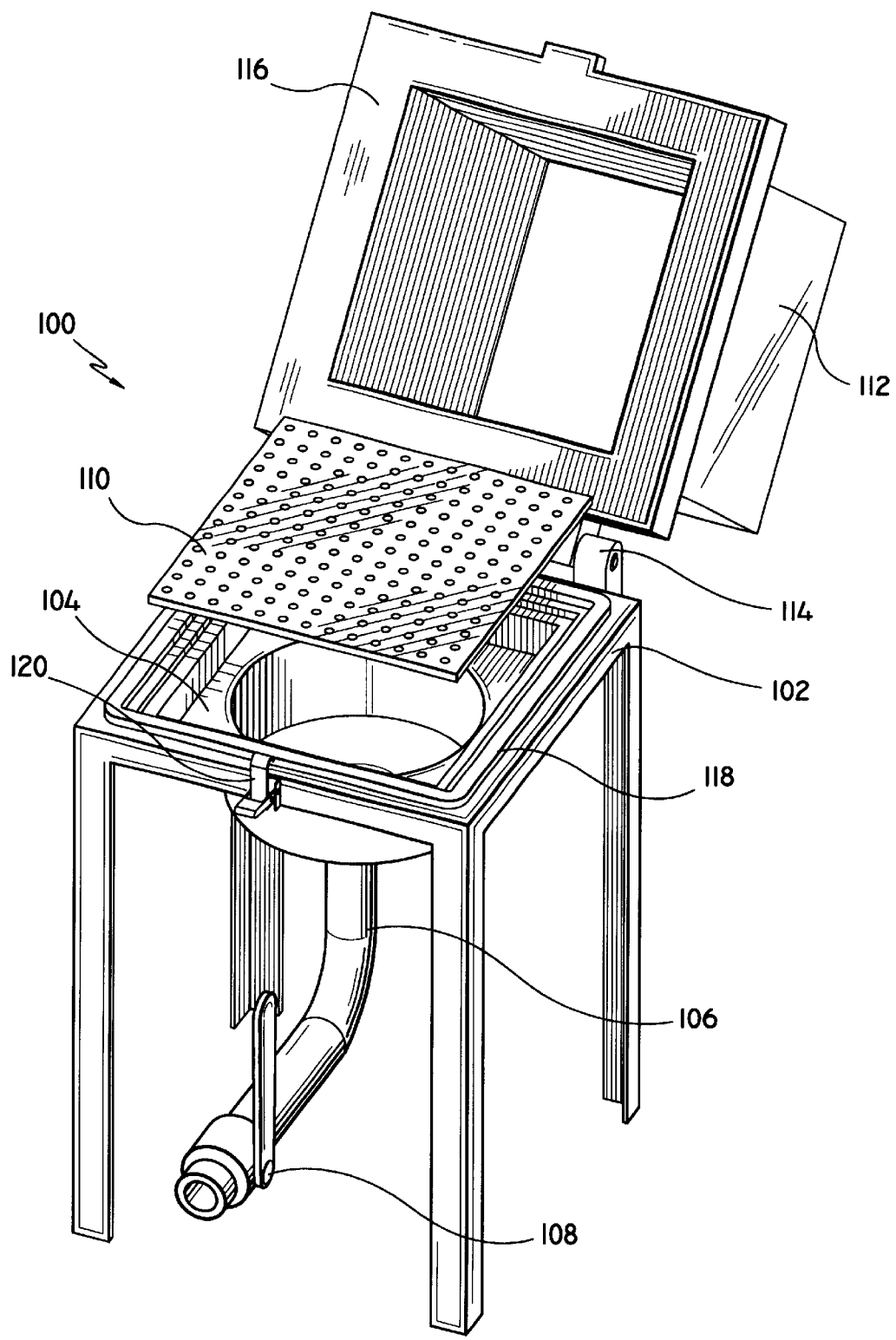
FIG. 2 is a perspective view of an apparatus utilized to shape the demineralized bone particles into a sheet-like configuration.
Figure 3:
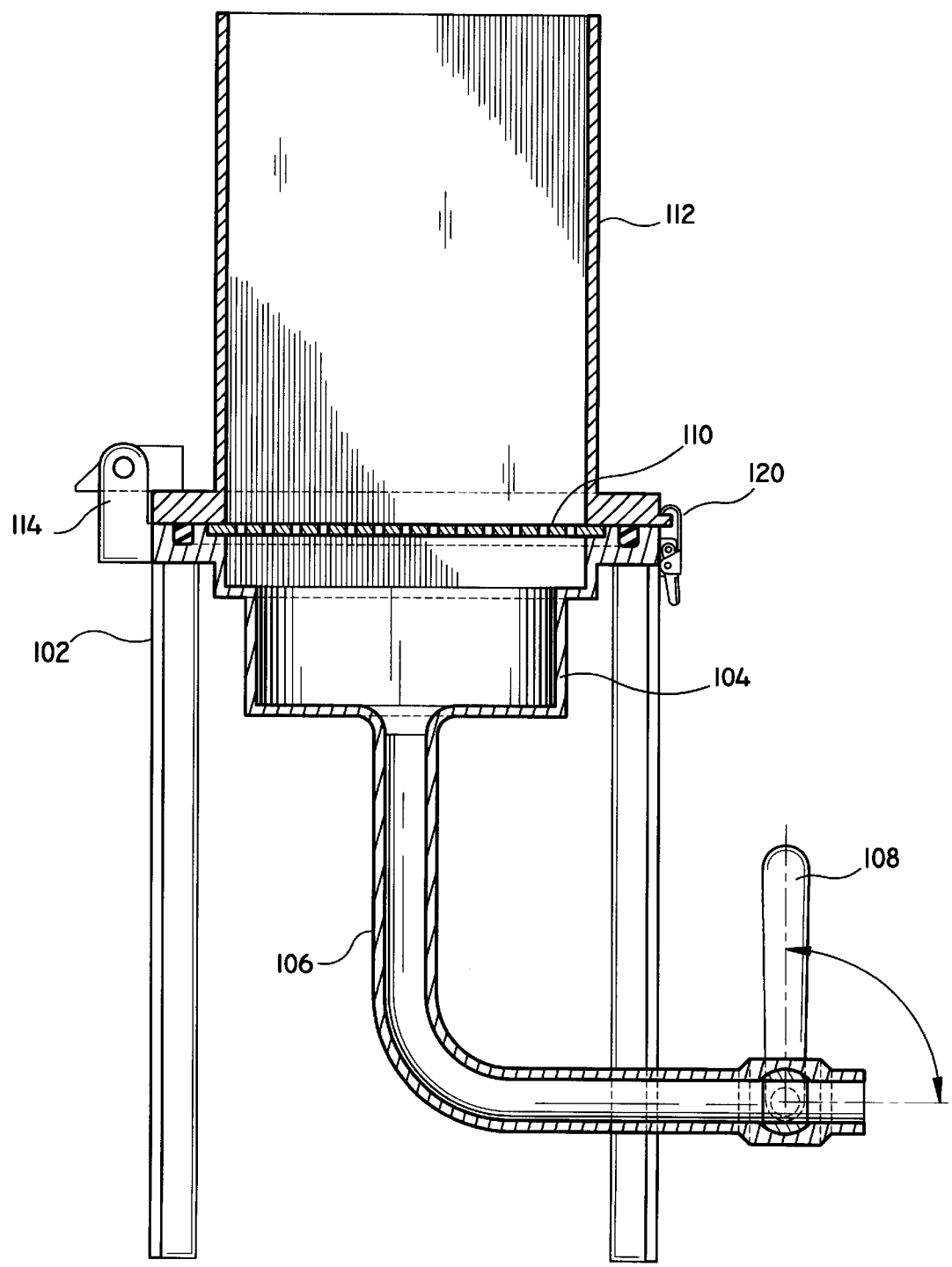
FIG. 3 is a side-sectional view of the apparatus of FIG. 2.

The bone slurry is then subjected to a shaping step or process 50 to establish the coherent shaped bone mass. In the preferred embodiment, the bone mass is shaped into a flat-sheet like configuration although, as stated above, other shapes including disks, cones, pins, screws, etc. are contemplated as well. An apparatus for forming the bone slurry into the sheet-configuration is depicted in FIGS. 2 and 3. This apparatus 100 includes a stand 102 having a basin 104 supported by a plurality of upstanding legs. A drain tube 106 extends from the lower surface of basin 102 and has an in-line valve 108. In-line valve 108 may be any conventional valve utilized to interrupt flow through tube 106 such as ball valves, gate valves, etc. A perforated stainless steel screen 110 is supported on the upper surface of stand 102. The screen 110 is replaceable.

The apparatus further includes a form tube 112 which is mounted by hinge 114 to stand 102. Form tube 112 pivots about hinge 114 between the open position depicted in FIG. 2 and the closed position depicted in FIG. 3. Form tube 112 has a peripheral flange 116 which is dimensioned to sit above the border of the screen 110 supported on the upper surface of stand 102. In the closed position of form tube 112, the peripheral flange 116 is compressed against the top surface of stand 102, sealingly securing the border of perforated screen 108 therebetween. As shown, stand 102 may have a peripheral elastomeric seal 118 to enhance sealing engagement of form tube 112 and the stand 102. A latch assembly 120 may be provided to releasably secure form tube 112 in the closed position. Any conventional latch assembly may be utilized. Form tubes having various shapes or dimensions may be employed with the apparatus.

To continue the process, the liquid slurry containing the demineralized elongated bone particles is poured into form tube 112. At such time, in-line valve 108 is in a closed condition to prevent discharge from the apparatus. Valve 108 is opened, and the liquid from the slurry drains through perforated screen 110, leaving a wetted layer of bone particles on the screen. This procedure is referred to herein as "wet-laying". It is to be noted that the bone particles are advantageously uniformly deposited on perforated screen 110 thereby forming a layer of bone material having a constant or uniform thickness. Thereafter, latch assembly 118 mounted to form tube 112 is opened and perforated screen 110 is then removed.

The layer of wetted bone particles removed from apparatus 100 is blotted dry using an absorbent material. A compressive force or weight may be applied to the absorbent material to facilitate drying of the bone particles. A sheet of Tyvek may be placed on top of the layer of bone particles for support and the screen is turned over and removed to expose the other surface of the wetted bone particles. This side is then blotted dry in the manner discussed above and a sheet of Tyvek is placed on the surface. At such a time, the bone sheet is sandwiched between two Tyvek sheets.

The result of the wet-laying procedure with apparatus 100 is the shaping of the demineralized bone particles to provide a coherent sheet of bone particles. The thickness of the layer of wetted bone particles can vary widely and is dependent upon the amount of bone slurry deposited into the form tube. Either before or after the wet-laying procedure, one or more additional substances can be added to the bone particles, e.g., thixotropic agents, therapeutic agents, and the like as previously mentioned.

Warming of Bone Sheet

Figure 4:
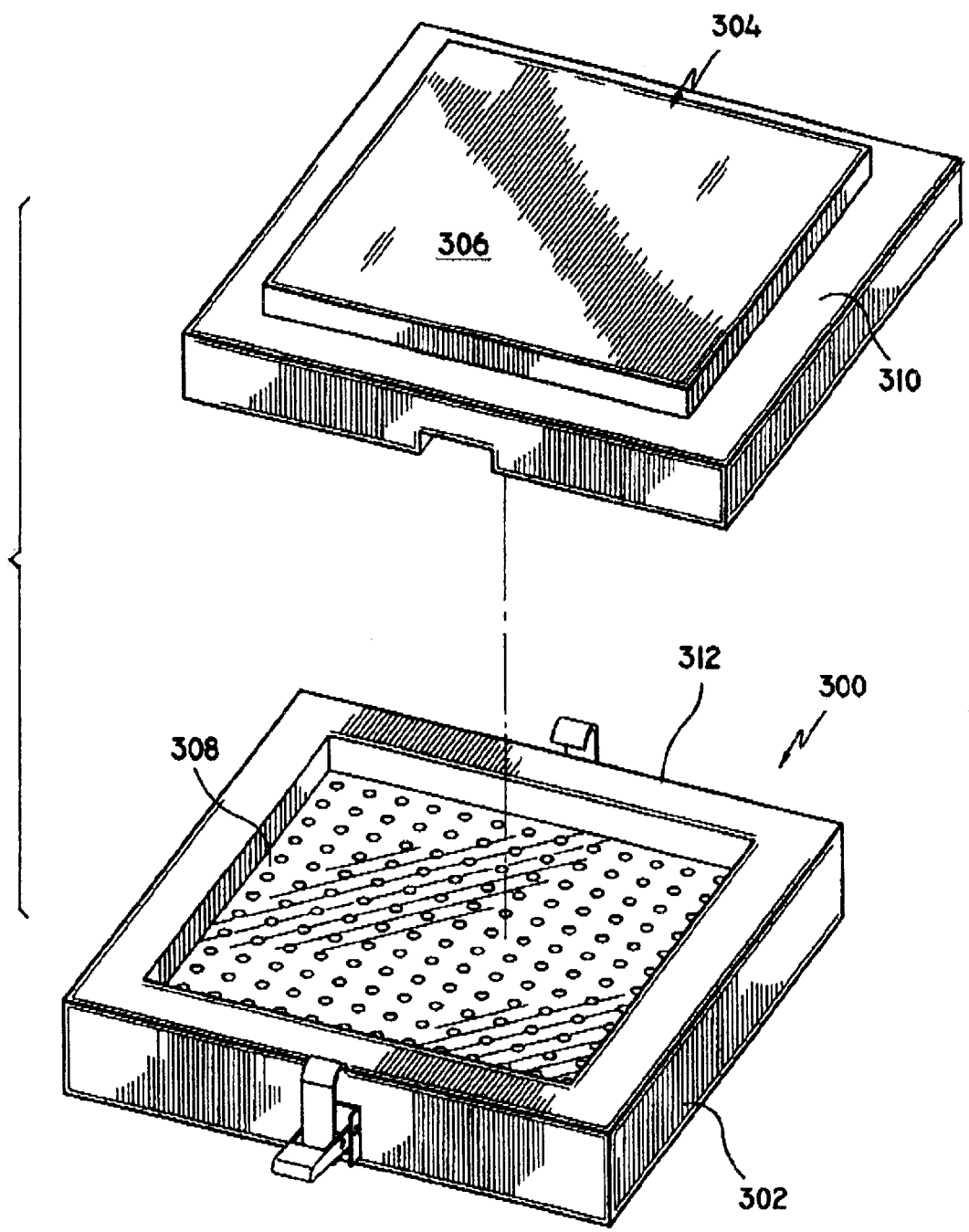
FIG. 4 is a perspective view of a sheet mold utilized to hold the sheet of demineralized bone particles during the warming process.
Figure 5:
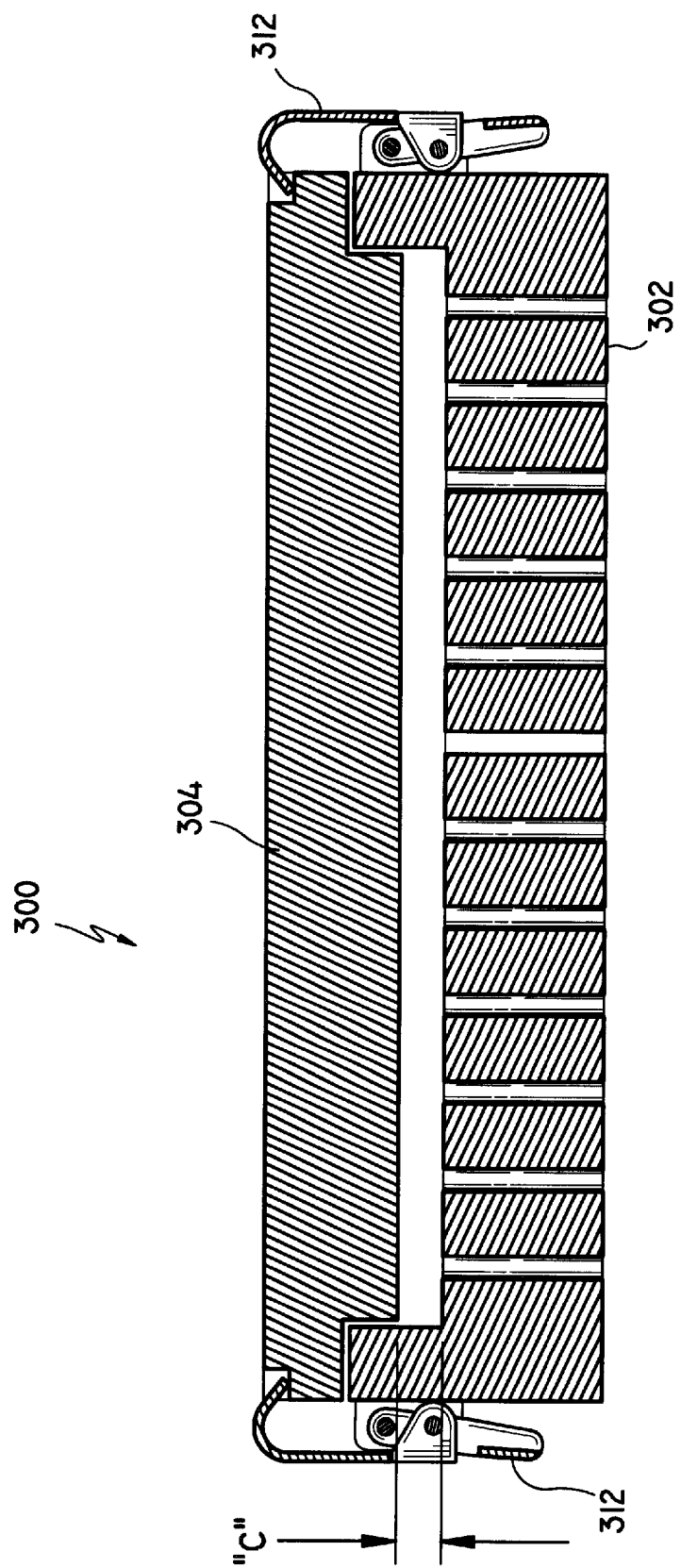
FIG. 5 is a side-sectional view of the sheet mold of FIG. 4.

Subsequent to forming of the bone sheet, the bone sheet is prepared for warming 60. With reference to FIGS. 4 and 5, the formed bone sheet (with or without the Tyvek sheets) is preferably positioned within a sheet mold 300. Sheet mold 300 includes a perforated polypropylene base 302 and solid metallic lid 304 which is mountable to the base 302. In FIG. 4, solid lid 304 is shown disassembled from base 302 and inverted. Solid lid 304 includes inner raised portion 306 which is accommodated within an inner recess 308 of base 302 when in the assembled condition whereby peripheral ledge 310 of the lid 304 rests on shelf 312 of the base 302. Metallic lid 304 is made from stainless steel, although, any conductive metallic material could be used as well.

As best depicted in FIG. 5, solid lid 304 when mounted to base 302 defines a gap or clearance "c" between the surfaces of the lid 306 and the base 302. The gap or clearance preferably approximates the thickness of the bone sheet which is to be positioned therein.

In accordance with the heating step, the bone sheet is initially placed into base 302 and the metallic lid 304 is secured thereto with the use of latches 312. Latches 312 may be any conventional latch suitable for this purpose. It is to be appreciated that solid lid 104 exerts a slight compressive force on the bone sheet thereby ensuring a constant thickness of the bone sheets over multiple uses. The mold 300 with bone sheet is then placed into a heating chamber such as an oven, a lyophilizer (with no vacuum applied) or a warming plate and the bone sheet is warmed for a predetermined time at a controlled temperature. In a preferred embodiment, the bone sheet is warmed for a period ranging from about 2 hrs. to about 4 hrs., more preferably, 3 hrs., at a temperature ranging from about 25° to about 55° C., most preferably, about 45° C. During warming some moisture evaporates from the bone sheet through the perforations of base 302. Compression of the bone sheet by lid 304 facilitates this evaporation and/or drainage as well.

In the preferred embodiment, the bone sheet is at least partially warmed through conductive heat transfer by the metallic plate. It is envisioned that the bone sheet may be heated without the use of the mold through direct heating methods or alternatively the metallic lid may be subjected to heat energy whereby the bone sheet is heated solely through conductive transfer through the lid. Alternate sources of heat energy include microwave, radio-frequency, laser, etc.

The warmed bone sheet is thereafter removed from the heating device. Upon its removal, the sheet is in a flexible and pliable condition. It is to be appreciated that the heating step advantageously improves the capacity of the bone sheet to maintain its cohesive properties and, in addition, it minimizes bone particle disassociation thereof, particularly, upon rehydration.

Drying of Bone Sheet

Figure 6:
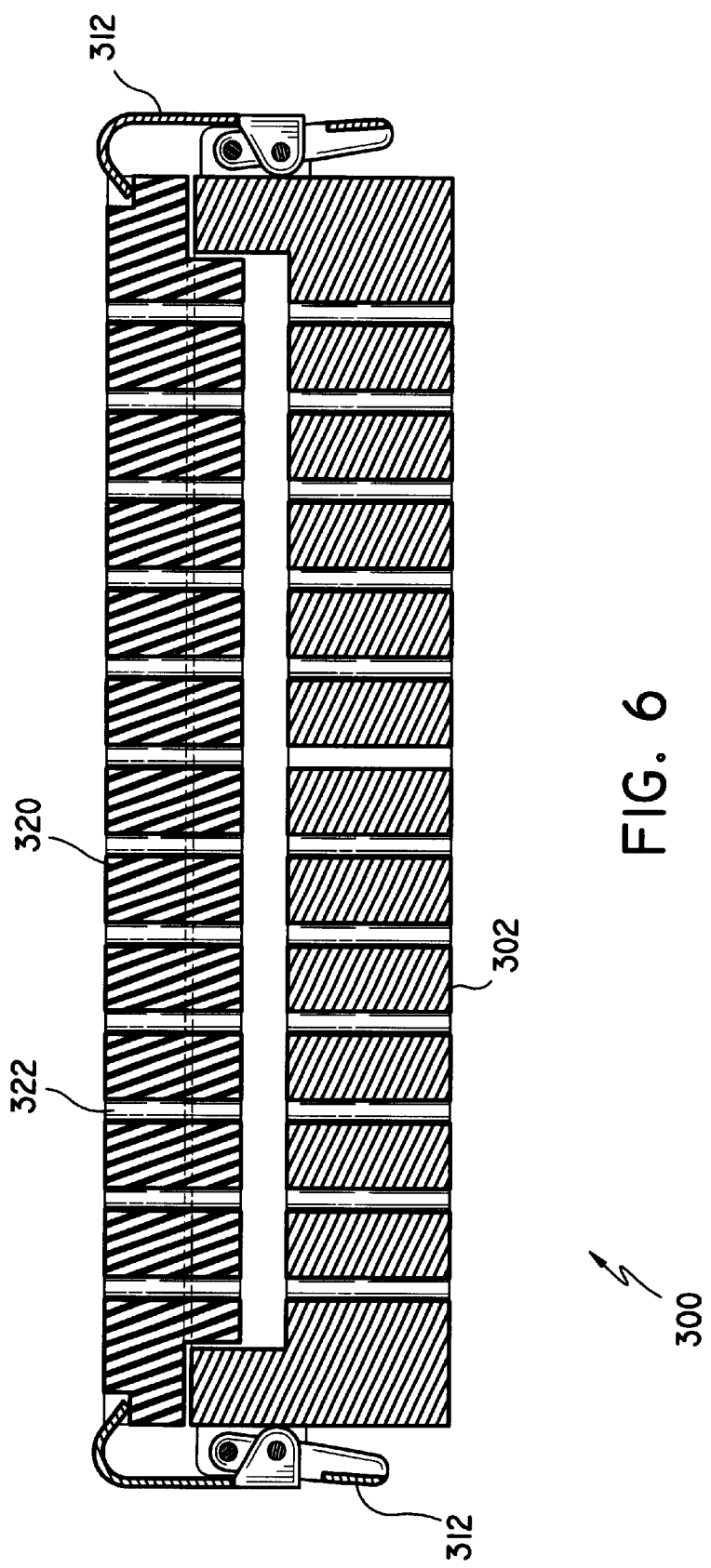
FIG. 6 is a side-sectional view of the sheet mold with a polypropylene lid.

The wet demineralized bone particles may then be optionally subjected to drying step 70, preferably by lyophilization in accordance with procedures and conditions that are well known in the art, e.g., a shelf temperature of from about −20 to about −60° C., a vacuum of from about 150 to about 100 mTorr for a time of from about 4 to about 48 hours depending on the bone mass. With reference to FIG. 6, metallic lid 304 is removed from base 302 and a polypropylene lid 320 is mounted to the base 302. Polypropylene lid 320 is identical in configuration to metallic lid but includes perforations 322 to permit escape of moisture therethrough during lyophilization. Once polypropylene lid 322 is mounted to base 302 and latched shut through latches 312, the mold 300 is placed in the lyophilizer apparatus. Upon completion of the lyophilization, polypropylene lid 320 is removed permitting the removal of the bone sheet. The resulting shaped sheet is rigid and relatively strong when dry and flexible and pliable when wetted or hydrated.

At the site of implantation, the shaped article can be employed in the dry state or, where site conformation is desired, in the hydrated state. The dry or hydrated article can be cut or sized if need be to conform to a site being repaired. The article can be hydrated with a suitable biocompatible liquid, e.g., water, saline solution, etc., for a period of time ranging from about 1 to about 120 minutes depending on the density of the shaped material. After being hydrated, the shaped material becomes flexible yet retains its shape and much of its strength. The shaped material of this invention can be packaged in either the dried or wet state and stored for subsequent application. In some circumstances, it is preferable to package the material in the wet state so that it is ready for immediate use at the surgical site.

The shaped materials of this invention can be utilized in a wide variety of orthopaedic, neurosurgical and oral and maxillofacial surgical procedures such as the repair of simple and compound fractures and non-unions, external and internal fixations, joint reconstructions such as arthrodesis, general arthroplasty, cup arthroplasty of the hip, femoral and humeral head replacement, femoral head surface replacement and total joint replacement, repairs of the vertebral column including spinal fusion and internal fixation, tumor surgery, e.g. deficit filling, discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts, etc. These materials can be sutured or stapled in place for anchoring purposes and serve in guided tissue regeneration or as barrier materials.

The bone sheet produced in accordance with the process of the present invention (i.e., utilizing the warming step) exhibits enhanced capacity to maintain its cohesive properties and minimal bone particle disassociation upon rehydration. Consequently, product handling and application at the operative site is enhanced.

It will be understood that various modifications may be made to the embodiment disclosed herein. For example, various lengths and types of sutures may be employed. Therefore, the above description should not be construed as limiting but merely as an exemplification of a preferred embodiment. Those skilled in the art will envision other modifications within the scope and spirit of the claims appended hereto.

What is claimed is:

1. A process for fabricating shaped material from bone particles, comprising the steps of:

applying a liquid slurry of bone particles to a support;

removing excess liquid from the slurry of bone particles to provide a coherent shaped mass of bone particles;

warming the shaped-mass of bone particles at a predetermined temperature and for a predetermined time period to improve cohesive properties of the shaped-mass of bone particles; and subjecting the shaped-mass of demineralized bone particles to lyophilization subsequent to the step of warming.

2. The process according to claim 1 wherein the step of applying includes applying a liquid slurry comprises demineralized bone particles.

3. The process according to claim 2 further including the step of compressing the shaped-mass of demineralized bone particles during the step of warming.

4. The process according to claim 2 wherein the step of applying includes pouring the liquid slurry of demineralized bone particles onto a porous support to provide a sheet of demineralized bone particles.

5. The process according to claim 4 further including the step of positioning the sheet of demineralized bone particles into a correspondingly dimensioned porous mold support.

6. The process according to claim 5 wherein the step of warming includes placing the mold support and the sheet of demineralized bone particles into a heating device.

7. The process according to claim 2 wherein the step of applying includes applying a liquid slurry of demineralized bone particles, wherein the bone particles are selected from the group consisting of cortical, cancellous and corticocancellous bone, and wherein the bone particles have an autogenous, allogenic or xenogeneic origin.

8. The process according to claim 2 wherein the step of warming includes subjecting the shaped mass of demineralized bone particles to a temperature ranging from about 22° C. to about 55° C. for a period of time ranging from about 2 hours to about 4 hours.

9. The process according to claim 8 wherein the step of warming includes subjecting the shaped mass of demineralized bone particles to a temperature of about 45° C. for a period of time about 3 hours.

10. The process according to claim 9 wherein the step of lyophilizing further includes positioning the sheet of demineralized bone particles disposed in the mold within a lyophilization chamber.

11. The process according to claim 9 further including the step of compressing the sheet of demineralized bone particles while subjecting the sheet to heat.

12. The process according to claim 11, wherein the step of compressing includes placing a compressive cover on to the mold to apply compressive forces to the sheet of demineralized bone particles disposed therein.

13. A method for treating a shaped-mass of demineralized bone particles, comprising the steps of:

heating a shaped-mass of demineralized bone particles; and subsequently lyophilizing the shaped-mass of demineralized bone particles; wherein, during the step of heating, the shaped-mass of demineralized bone particles are subjected to an elevated temperature for a predetermined period of time sufficient to improve the cohesive characteristics of the shaped-mass of bone particles upon lyophilization thereof.

* * * * *